J. Young,
Washing Machine,
No. 1,216.
Fig. 1. Reissued July 30, 1861.
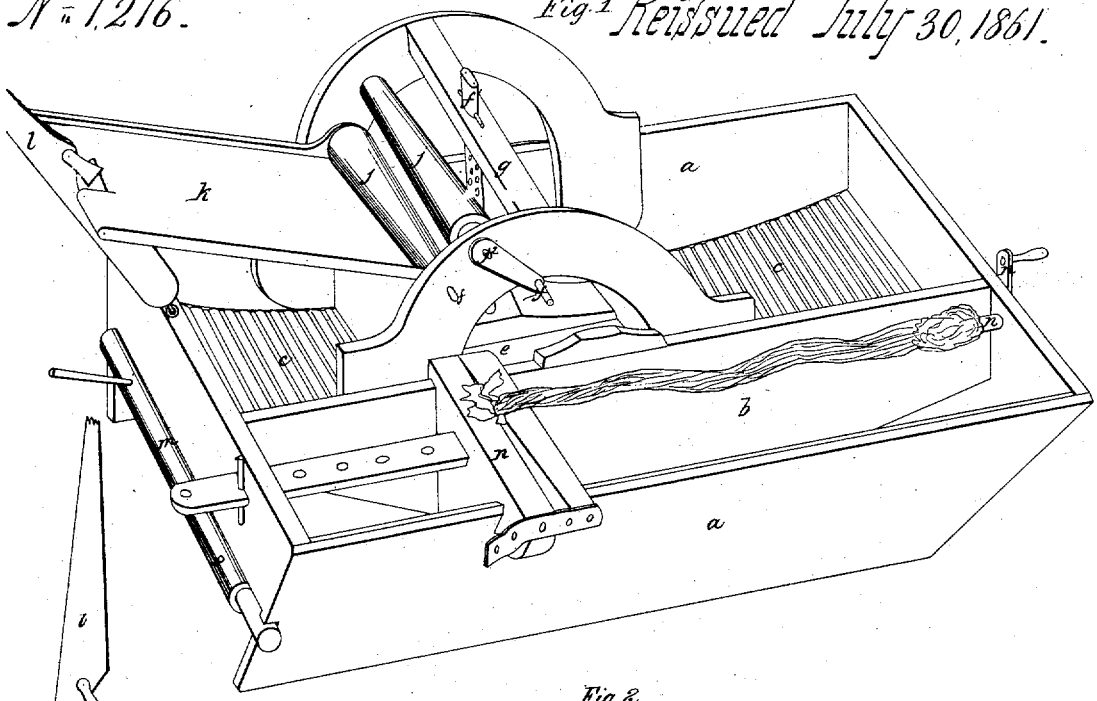
Fig. 2.
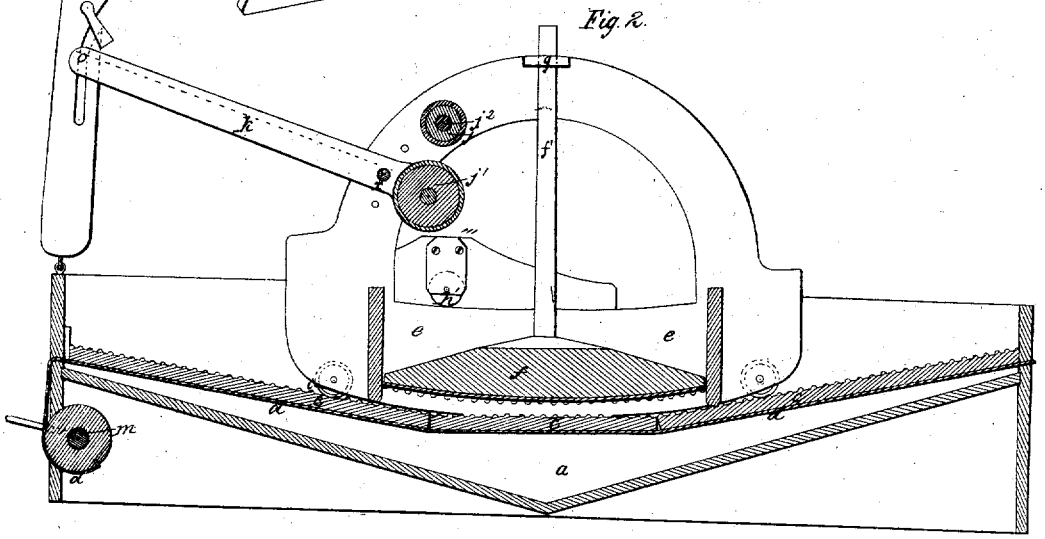
N. PETERS, PHOTO-LITHOGRAPHER, WASHINGTON, D. C.

UNITED STATES PATENT OFFICE.

JOHN YOUNG, OF WEST GALWAY, NEW YORK.

IMPROVEMENT IN WASHING-MACHINES.

Specification forming part of Letters Patent No. 5,788, dated September 19, 1848; Reissue No. 1,216, dated July 30, 1861.

*To all whom it may concern:*

Be it known that I, JOHN YOUNG, of West Galway, in the county of Fulton and State of New York, have invented a new and useful Improvement in Machines for Washing and Wringing Clothes; and I do hereby declare the following to be a full, clear, and exact description thereof, reference being had to the accompanying drawings, figures, and letters of reference thereon, making part of this specification.

Of the said drawings, Figure 1 is a perspective view, and Fig. 2 a vertical longitudinal section.

Similar letters of reference indicate like parts in all the drawings.

The nature of the first part of my invention consists in the employment of a flexible fluted board made in segments and suspended upon a cord, strap, or other flexible support and combining therewith elastic rollers properly mounted for wringing and squeezing the clothes.

The nature of the second part of my invention consists in the employment and use of elastic rollers which shall readily yield for any inequalities in the clothes passing through them, and to prevent injury thereto, as will be more fully set forth.

The nature of the third and last part of my invention consists in the employment of the conical-shaped rollers for producing a rubbing as well as squeezing motion on the clothes passing between them, as will be fully described and set forth.

To enable others skilled in the art to make and use my invention, I will proceed to describe its construction and operation.

In the accompanying drawings, the box *a*, to contain the suds and clothes, may be made of any suitable form, having through its middle a vertical division-board, *b*, for the purpose of separating the rubbing from the wringing apparatus. The wash-board *c* is made in segments, which are suspended on a cord, *d*, either passing through or beneath them. The upper surface of these segments are fluted in the manner of a common wash-board. Upon this wash-board is placed a rubbing-box, *e*, which runs on friction-wheels *e*, which rest in grooves parallel to the sides and formed in the flexible washboard, into which the clothes to be washed are placed. Upon the clothes so placed in the box a follower, *f*, is put to press them down, which follower has a stem, *f'*, projecting upward to the cross-piece *g*, through which it passes. The rubbing-box is held in its position by the friction-rollers *h h*, which are placed on the sides of the box for this purpose. On the sides of this rubbing-box the arched frames are raised, which are connected on the top by the cross-piece *g*. The follower *f* is held down upon the clothes by passing a pin through its stem beneath the cross piece *g*. Between these arches the conical squeezing-rollers *j j'* are placed, the roller *j* turning on its axis, which rests in suitable bearings formed in the side pieces of the turning-platform *k*. The joint pin *x*, on which the platform turns, is placed to one side and below the bearing of the axis $j^2$ of the upper roller, *j*, in order that the rollers may open and shut like a pair of pinchers, to lay hold of and squeeze the water out of the clothes. The rollers are covered with gum-elastic, india-rubber, or similar material, to prevent injury to the clothes as they pass through.

The conical shape of the rollers causes them while acting together to produce a lateral and forward rub as well as squeeze of the clothes, for one being driven by the other, and the parts in contact being of changing relative diameter throughout the entire length, the driver tends to move the driven slower than itself at one end and faster at the other, thus causing constant though slight rubbing of the clothes in conjunction with the squeeze, which greatly accelerates the operation of washing.

The rubbing-box is moved backward and forward by the lever *l*, which is hinged at its lower end to the upper edge of the tub. The lever is joined to the hinged platform *k*, which serves the double purpose of a connecting-rod and conveyer on which the washed clothes slide down by their gravity into a basket or other receptacle placed to receive them whenever the outer end of the same is detached from the lever *l* and dropped for that purpose. The wash-board *c* is raised up by tightening the cords on which it rests, which is done by turning the windlass *m*, to which these cords are connected.

The apparatus *n*, shown in Fig. 2, is of ordinary construction, forms no part of my invention, and therefore needs no particular description.

After placing in the box *a* the desired quantity of suds, the clothes are put into the rubber-box and the follower forced down upon them. The operator then lays hold of the lever and moves the box back and forth with it until the clothes are sufficiently rubbed. The follower is then taken out and the clothes drawn through between the rollers *j j'*, sufficient pressure being applied to the outer end of the hinged platform to press the rollers together with a force adequate to express the water from the clothes.

I claim—

1. The combination of the rollers with the hinged platform for the purpose of rubbing the clothes and squeezing the water therefrom, substantially as and for the purposes described and specified.

2. The employment and use of elastic rollers which shall readily yield to any inequalities in the clothes passing through them, and thereby prevent injury, substantially as and for the purposes specified.

3. The employment of the conical rollers for producing a rubbing as well as squeezing motion on the clothes passing between them, whereby the operation of washing is greatly accelerated, substantially as and for the purposes described and specified.

JOHN YOUNG.

Witnesses:
JAMES YOUNG,
LAUREN O. KENNEDY.